United States Patent
Neo et al.

(10) Patent No.: US 9,642,569 B2
(45) Date of Patent: May 9, 2017

(54) SYRINGE WITH REMOVABLE PLUNGER FOR ARTERIAL BLOOD GAS SAMPLE COLLECTION

(71) Applicant: Becton, Dickinson and Company, Franklin Lakes, NJ (US)

(72) Inventors: Kevin Wei Li Neo, Singapore (SG); Chee Mun Kuan, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 194 days.

(21) Appl. No.: 14/351,017

(22) PCT Filed: Oct. 18, 2012

(86) PCT No.: PCT/US2012/060778
§ 371 (c)(1),
(2) Date: Apr. 10, 2014

(87) PCT Pub. No.: WO2013/059429
PCT Pub. Date: Apr. 25, 2013

(65) Prior Publication Data
US 2014/0296744 A1  Oct. 2, 2014

Related U.S. Application Data

(60) Provisional application No. 61/549,536, filed on Oct. 20, 2011.

(51) Int. Cl.
*A61B 5/15* (2006.01)
*A61B 5/153* (2006.01)

(52) U.S. Cl.
CPC .... *A61B 5/150572* (2013.01); *A61B 5/15003* (2013.01); *A61B 5/153* (2013.01);
(Continued)

(58) Field of Classification Search
CPC ... A61B 5/1405; A61B 5/1411; A61B 5/1438; A61B 5/15003; A61B 5/150236;
(Continued)

(56) References Cited

U.S. PATENT DOCUMENTS 2,688,325 A * 9/1954 Lockhart ............. A61B 5/1405
604/220
3,577,980 A 5/1971 Cohen
(Continued)

FOREIGN PATENT DOCUMENTS

AU  552883  11/1981
CN  201939348 U  8/2011
(Continued)

*Primary Examiner* — Michael C Stout
(74) *Attorney, Agent, or Firm* — The Webb Law Firm

(57) ABSTRACT

A fluid collection assembly (10) and method for use thereof is provided including a fluid collection cartridge (20) having a tubular member (21) with a plunger assembly slidably inserted. The plunger assembly includes a stopper (32) and a plunger rod (31). The stopper and plunger rod are removably interlocked together which enables the plunger rod to exert a force in a distal direction on the stopper and to be removed from the stopper upon the application of a proximal force thereto. The fluid collection assembly is particular useful in the collection of arterial blood. In use, the assembly is primed with a liquid anticoagulant, the plunger rod is removed, and a blood sample is collected with the arterial pressure causing the stopper to travel in a proximal direction along the cartridge.

23 Claims, 9 Drawing Sheets

(52) U.S. Cl.
CPC .. *A61B 5/150236* (2013.01); *A61B 5/150244* (2013.01); *A61B 5/150389* (2013.01); *A61B 5/150496* (2013.01); *A61B 5/150587* (2013.01); *A61B 5/150717* (2013.01); *A61B 5/150732* (2013.01); *A61B 5/150755* (2013.01); *A61B 5/150824* (2013.01); *A61B 5/150893* (2013.01)

(58) Field of Classification Search
CPC ........ A61B 5/150244; A61B 5/150496; A61B 5/150572; A61B 5/153; A61B 5/154; A61B 17/3494; A61B 5/150351; A61M 5/31515; A61M 5/3202; A61M 5/3213; A61M 5/3243; A61M 5/24; A61M 5/315; A61M 5/31511; A61M 2005/3121; A61J 1/201; A61J 1/2013; A61J 1/2096; B01L 2400/0478; B01L 3/0217
See application file for complete search history.

(56) References Cited

U.S. PATENT DOCUMENTS

| | | | |
|---|---|---|---|
| 3,645,253 A | | 2/1972 | Goverde et al. |
| 3,930,492 A | * | 1/1976 | Hatsuno .............. A61B 5/1416 600/577 |
| 4,372,325 A | | 2/1983 | Raitto |
| 4,821,738 A | | 4/1989 | Iwasaki et al. |
| 5,030,208 A | * | 7/1991 | Novacek .................. A61L 2/28 604/110 |
| 5,314,416 A | | 5/1994 | Lewis et al. |
| 5,324,266 A | * | 6/1994 | Ambrisco ............ A61B 5/1427 604/125 |
| 5,377,689 A | | 1/1995 | Mercereau |
| 5,415,648 A | | 5/1995 | Malay et al. |
| 5,529,378 A | | 6/1996 | Chaban et al. |
| 5,755,701 A | * | 5/1998 | Sarstedt ............. A61B 5/15003 600/576 |
| 7,125,394 B2 | * | 10/2006 | Berman ................ A61M 31/00 604/15 |
| 8,075,522 B2 | * | 12/2011 | Larsen .................. A61M 5/326 604/110 |
| 8,092,425 B2 | * | 1/2012 | Bobst .................. A61M 5/5086 604/111 |
| 2004/0043505 A1 | | 3/2004 | Walenciak et al. |
| 2010/0076378 A1 | * | 3/2010 | Runfola ............. A61M 5/3234 604/110 |

FOREIGN PATENT DOCUMENTS

| | | |
|---|---|---|
| EP | 1543771 A1 | 6/2005 |
| FR | 2300538 A1 | 9/1976 |
| GB | 2218076 A | 11/1989 |
| JP | 4815910 | 5/1973 |
| JP | 5146316 | 11/1976 |
| JP | 5991944 A | 5/1984 |
| JP | 61113431 A | 5/1986 |
| WO | 88/02238 A1 | 4/1988 |

* cited by examiner

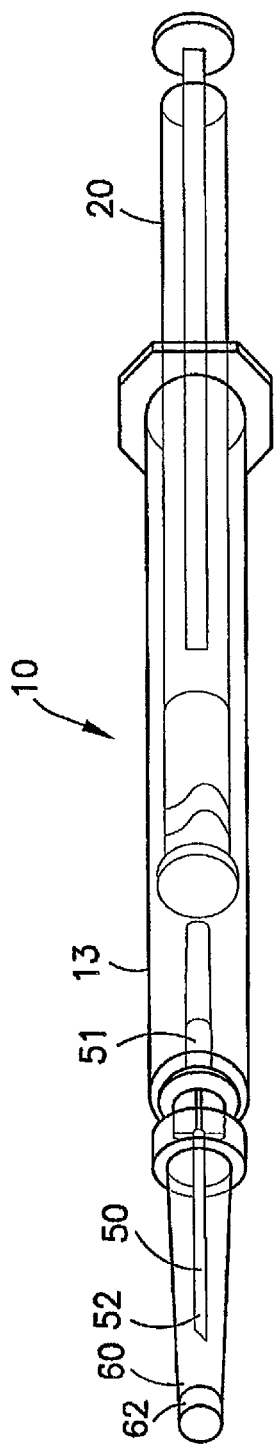
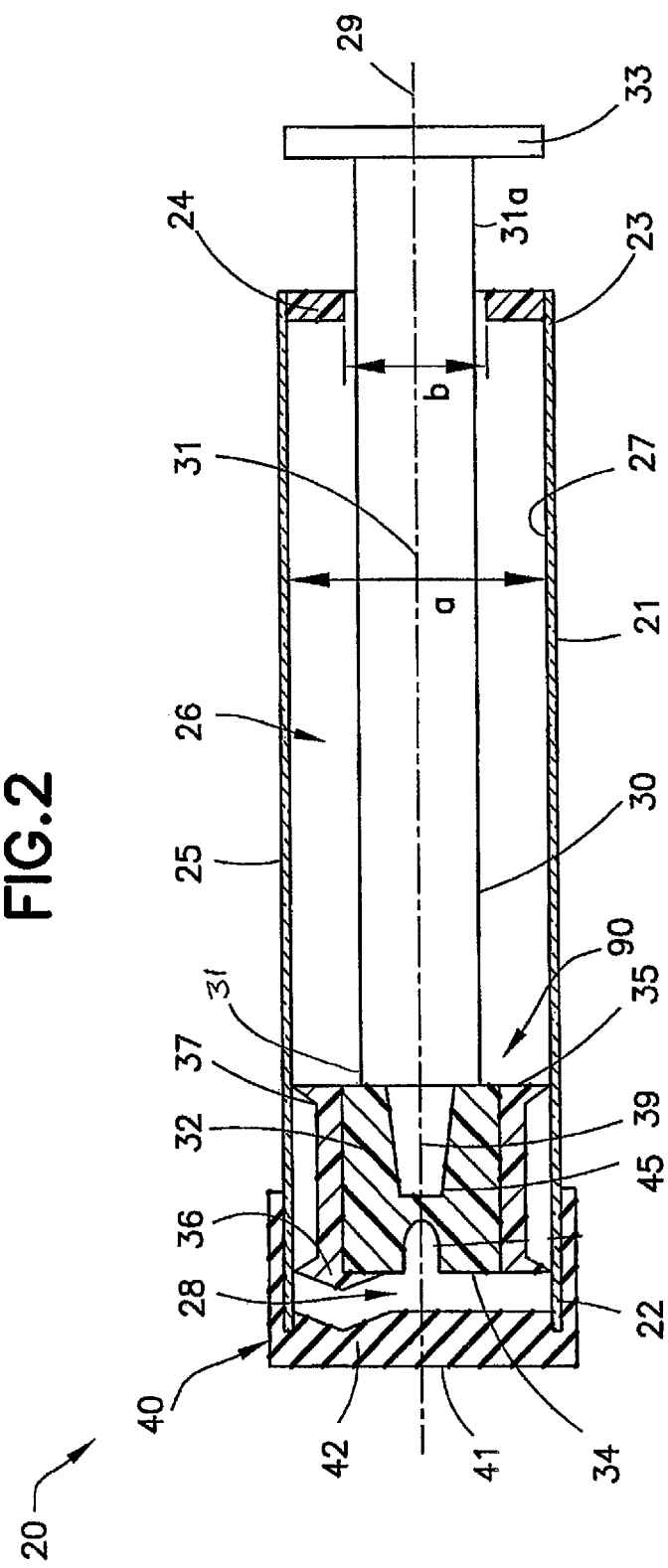

SYRINGE WITH REMOVABLE PLUNGER FOR ARTERIAL BLOOD GAS SAMPLE COLLECTION

CROSS-REFERENCE TO RELATED APPLICATIONS

This application is the United States national phase of International Application No. PCT/US2012/060778 filed Oct. 18, 2012, and claims priority to U.S. Provisional Patent Application No. 61/549,536 filed Oct. 20, 2011, the disclosures of which are hereby incorporated in their entirety by reference.

BACKGROUND OF THE INVENTION

Field of the Invention

The present invention is directed to a fluid collection assembly and methods for use thereof, and more particularly, to a fluid collection assembly having a removable plunger rod for use in the collection of a fluid sample, such as for collection of an arterial blood sample.

Description of Related Art

Arterial blood collection syringes are used for withdrawing and collecting arterial blood samples from the body of a patient. Once the blood sample is collected, it is subjected to diagnostic analysis for gases, electrolytes, metabolites, and other elements that are indicative of a condition of a patient. Various types of syringes have been devised for collecting arterial blood samples, which mainly comprise elements from a hypodermic syringe, i.e., a plastic or glass syringe barrel, a sealing elastomeric stopper, and a plunger rod. Additionally, certain arterial blood collection syringes include a self-sealing filter that allows passage of air out of the syringe during blood collection, while still preventing the passage of blood. This latter type of syringe having a filter allows for an arterial sample to be collected without the need to aspirate the syringe, as is required with a syringe having a plunger rod and a plunger stopper.

Typical arterial blood collection syringes include a two-piece plunger rod assembly comprised of an elastomeric sealing stopper attached to a plunger rod. U.S. Pat. No. 5,314,416 to Lewis et al. discloses a low friction syringe assembly having a typical two-piece plunger rod and a plunger tip assembly. The sealing stopper and plunger rod must be assembled together in a separate operation prior to assembly with a syringe barrel. In addition, a silicone lubricant is usually used on the interior wall of the syringe barrel or the sealing stopper is composed of a self-lubricating polymeric material to facilitate easy slidable movement of the elastomeric sealing stopper against the interior wall of the syringe barrel. Such syringes typically involve an active step for obtaining a blood sample. For example, a needle connected to such a syringe accesses a patient's blood vessel, and the syringe is thereafter aspirated by the user holding the syringe with one hand and drawing the plunger rearwardly within the syringe barrel with the other hand so as to draw a blood sample into the syringe barrel for analysis. The need for the user to use two hands during the blood sample collection introduces unnecessary movement during the blood draw process and possibly causing discomfort to the patient.

Arterial blood samples can also be obtained passively through the use of a syringe having a plunger with a porous filter to collect blood by way of the blood pressure of a patient from whom the blood is being collected. In such a syringe, the plunger mechanism is typically hollow, and includes a porous filter therein. A separate elastomeric sealing stopper is typically attached to the front end of the plunger mechanism for sealing within the syringe barrel, with air channels in the stopper for air passage through the filter. In use, the plunger is set at a certain position against a graduated scale of the syringe barrel, so that the desired volume of the sample to be collected is represented by the cavity within the syringe. Once a blood vessel of a patient is accessed by an appropriate needle attached to the syringe, arterial blood will fill the syringe under its own pressure. As the cavity within the syringe fills, air within the syringe is allowed to escape from the syringe by way of a gas permeable filter. When the blood sample contacts the filter, the filter seals, thereby preventing escape of blood and ingress of air and other contaminants into the collected sample. U.S. Pat. No. 4,821,738 to Iwasaki et al. discloses an arterial blood gas syringe including a typical two-piece assembly for use. The arterial blood gas syringe is comprised of a plunger rod and an elastomeric sealing plug having channels formed in an upper surface for use in removing air as arterial blood is received in the syringe. The channels extend in a generally radial direction and converge near the center of a sealing plug to allow the passage of air to and through a filter element contained within the sealing plug. U.S. Pat. Nos. 5,377,689 and 5,529,738, both to Mercereau, disclose a sampling syringe including a plunger cap having an air permeable filter attached to a plunger rod, which is in slidable communication with the inner wall of a syringe barrel. However, the arterial blood collected using this type of syringe is exposed to air within the barrel interior of the syringe during the blood collection. This can affect the accuracy of the arterial blood gas analysis since oxygen and carbon dioxide can migrate into or out of the arterial blood sample depending on the partial pressure of gases in the arterial blood relative to atmospheric air.

After completion of the blood sample collection, the needle is removed and the syringe containing the collected blood sample is then transported to the laboratory. Typically, blood samples collected in blood collection tubes are transported through pneumatic tubes between the ward and laboratory. However, the plunger that is protruding from the syringe barrel makes handling and transportation of the arterial blood collection syringe difficult and special care has to be taken not to dislodge the plunger thus preventing pneumatic tube transportation and increasing the time and resources required to transport and analyze the collected blood sample.

It would be therefore desirable to provide an arterial blood collection assembly and method of use thereof which is compatible with current clinical practice and enables a single-handed blood collection technique, which does not expose the collected blood to atmospheric air prior to analysis for blood gas levels and allows the plunger to be removed to facilitate easier handling and transportation of the collected sample.

SUMMARY OF THE INVENTION

Generally, the present invention is directed to a fluid collection cartridge, a fluid collection assembly, and a method of collecting a fluid sample. The present invention has particular utility in the collection of arterial blood samples.

According to a first aspect, the invention is directed to a fluid collection cartridge configured for use with a needle holder for collecting a fluid sample. The fluid collection cartridge includes a tubular member having a proximal end, an open distal end, and sidewall extending between the proximal end and the distal end defining an internal chamber having an internal reservoir and a pierceable closure associated with the open distal end of the tubular member. The closure is configured to cooperate with the sidewall of the tubular member to sealingly close the open distal end. The fluid collection cartridge further includes a plunger rod assembly including a stopper and a plunger rod removably associated with one another by an interengaging arrangement. The interengaging arrangement is configured to enable the plunger rod to apply a distally directed force to the stopper and to enable removal of the plunger rod from the stopper and from the tubular member upon the application of a proximally directed force.

The internal reservoir is configured to contain a fluid treatment additive, such as anticoagulants, clotting agents, stabilization additives, and the like. According to one embodiment, the fluid sample can comprise an arterial blood sample and the fluid treatment additive can be an anticoagulant in liquid form.

The stopper is slidably positioned between the distal end and the proximal end of the tubular member in fluid-tight engagement with an inside surface of the sidewall. The stopper can be a low resistance stopper. The interengaging arrangement can be configured to only enable the stopper to move in a distal direction. The stopper can also be configured to move toward the proximal end of the tubular member upon the collection of a fluid sample in the internal reservoir. According to one embodiment, the stopper can include at least one sealing ring extending around an outer circumferential surface of the stopper. According to another embodiment, the stopper can include a first and second sealing ring extending around an outer circumferential surface of the stopper. The stopper can further include a mixing fin extending from a distal end thereof. The proximal end of the tubular member can include an annular flange extending into the fluid reservoir. The interengaging arrangement can include one of a male member and a female member extending from a distal end the plunger rod and one of a corresponding female member and a male member in a proximal face of the stopper configured to mate with the male member or female member of the plunger rod.

According to another aspect, the invention is directed to a fluid collection assembly including a fluid collection cartridge having a tubular member having a proximal end, an open distal end, and sidewall extending between the proximal end and the distal end defining an internal chamber having an internal reservoir, a pierceable closure associated with the open distal end of the tubular member wherein the closure is configured to cooperate with the sidewall of the tubular member to sealingly close the open distal end, and a plunger rod assembly including a stopper and a plunger rod removably associated with one another by an interengaging arrangement. The interengaging arrangement is configured to enable the plunger rod to apply a distally directed force to the stopper and to enable removal of the plunger rod from the stopper and from the tubular member upon the application of a proximally directed force. The fluid collection assembly further includes a needle assembly having a cannula including a distal end and a proximal end and a first needle shield covering the distal end and a holder associated with the needle assembly wherein the holder is configured for cooperating with the fluid collection cartridge for collecting a fluid sample.

According to one embodiment, the first needle shield can include an indicator tip. The internal reservoir is configured to contain a fluid treatment additive, such as an anticoagulant material. The indicator tip on the first needle shield is designed to change color upon contact with the fluid treatment additive. According to one embodiment, the distal end of the cannula can be configured to withdraw a blood sample from an artery and wherein the presence of arterial blood pressure in the internal reservoir during blood collection causes the stopper to move toward the proximal end of the tubular member.

According to another aspect, the invention is directed to a method of collecting a blood sample comprising providing a fluid collection assembly having a fluid collection cartridge including a tubular member having a proximal end, an open distal end, and sidewall extending between the proximal end and the distal end defining an internal chamber having an internal reservoir, a pierceable closure associated with the open distal end of the tubular member, wherein the closure is configured to cooperate with the sidewall of the tubular member to sealingly close the open distal end, and a plunger rod assembly including a stopper and a plunger rod removably associated with one another by an interengaging arrangement. The interengaging arrangement is configured to enable the plunger rod to apply a distally directed force to the stopper and to enable removal of the plunger rod from the stopper and from the tubular member upon the application of a proximally directed force. The fluid collection assembly also includes a needle assembly having a cannula with a distal end and a proximal end and a first needle shield covering the distal end, and a holder associated with the needle assembly wherein the holder is configured for cooperating with the fluid collection cartridge. The method also includes priming the fluid collection assembly with a fluid treatment additive, removing the plunger rod from the fluid collection cartridge, and collecting a fluid sample into the internal reservoir.

According to one embodiment, the fluid treatment additive can be an anticoagulant in a liquid form and the first needle shield can include an indicator tip. Priming of the fluid collection assembly further includes inserting the fluid collection cartridge into the holder such that the proximal end of the cannula pierces the pierceable closure, pushing the plunger assembly in a distal direction until the stopper contacts the pierceable closure, and observing a color change in the indicator tip upon contact of the tip with the fluid treatment additive, indicating that the fluid collection assembly is primed and ready for use.

Collecting a fluid sample into the internal reservoir further includes inserting the distal end of the needle assembly into a fluid source such that fluid flows into the internal reservoir and forces the stopper to travel in a proximal direction along a longitudinal axis of the tubular member, removing the fluid collection cartridge from the holder when the stopper contacts an annular flange extending into the internal reservoir, and removing the distal end of the needle assembly from the fluid source. The method can also include attaching a luer adapter to the distal end of the fluid collection cartridge.

BRIEF DESCRIPTION OF THE DRAWINGS

FIG. 2 is a perspective view of a fluid collection assembly in accordance with an embodiment of the present invention.

FIG. 3 is a partial cross-sectional side view of a fluid collection cartridge as similarly shown in FIG. 1 in accordance with an embodiment of the present invention.

DETAILED DESCRIPTION OF THE INVENTION

Figure 1:
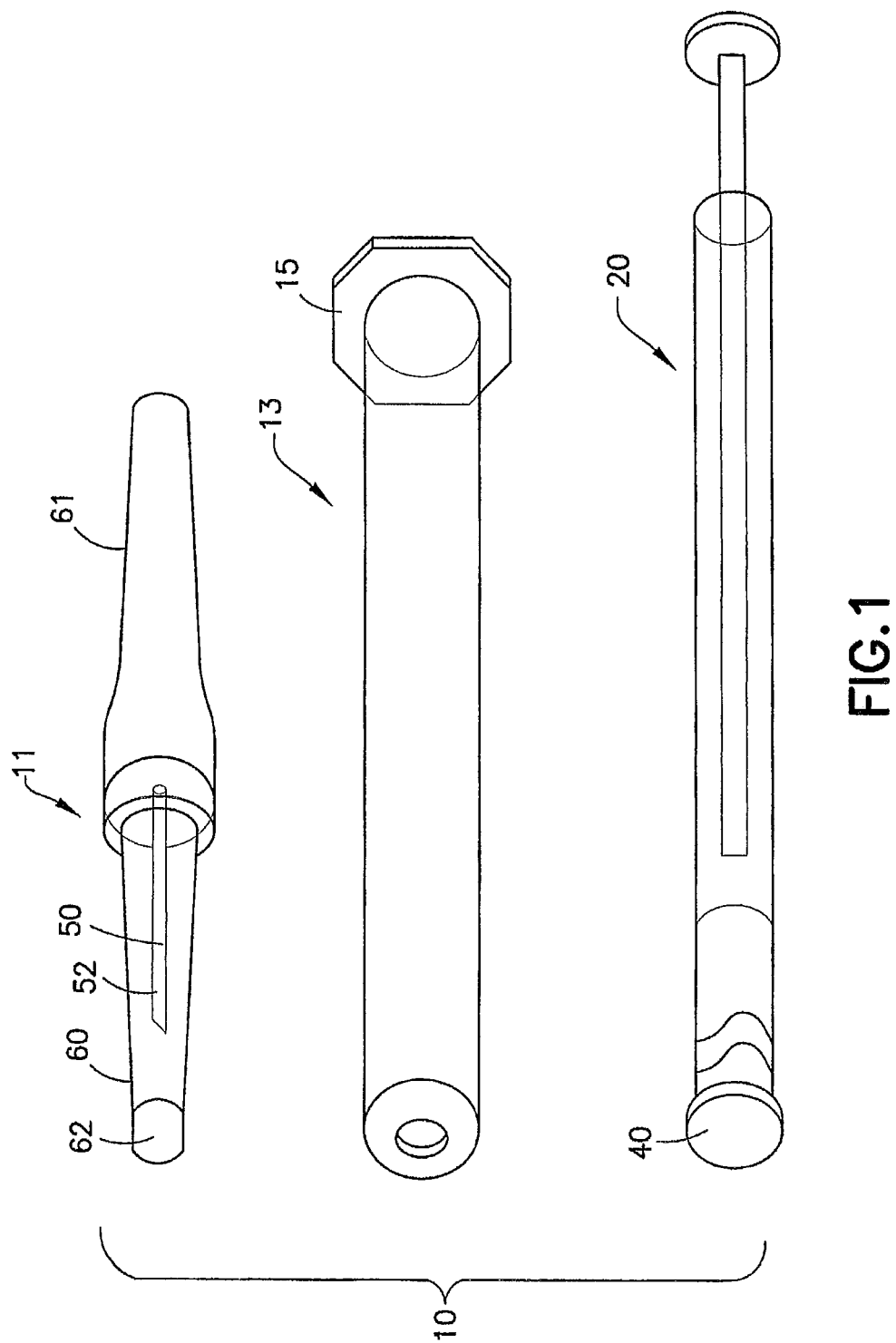
FIG. 1 is a perspective view of the components of a fluid collection assembly in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used herein, the term "proximal" refers to a location on the blood collection assembly according to the embodiments of this invention that, during normal use, is closest to the clinician using the device and farthest from the patient in connection with whom the device is used. Conversely, the term "distal" refers to a location on the blood collection assembly of this invention that, during normal use, is farthest from the clinician using the device and closest to the patient in connection with whom the device is used. Furthermore the term "proximal direction" indicates a direction of movement away from the patient and toward the user of the blood collection assembly, whereas the term "distal direction" indicates a direction of movement away from the user of the blood collection assembly and toward the patient.

Referring to the drawings, in which like reference characters refer to like parts throughout the several views thereof, FIGS. 1 and 2 illustrate a fluid collection assembly, generally indicated as 10, including a needle assembly, generally illustrated as 11, a first needle shield 60, a tube holder, generally indicated as 13, and a fluid collection cartridge, generally indicated as 20. According to one embodiment, the fluid collection assembly 10 can comprise an arterial blood collection assembly, and thus, the present invention is generally described in terms of an arterial blood collection assembly. While described herein in terms of an arterial blood collection cartridge 20 intended for use with a needle assembly 11, the cartridge 20 of the present invention may be used with or may incorporate other medical devices, such as another medical device assembly that includes a piercing element or allows for attachment to a catheter or arterial lines.

With continuing reference to FIGS. 1 and 2 and with reference to FIGS. 3-11, the primary components of the fluid collection cartridge 20 include a plunger assembly 30 having a removable plunger rod 31 and a stopper 32 in slidable communication with a tubular member 21 and a closure 40.

With particular reference to FIG. 3, a fluid collection cartridge 20 according to an embodiment of the invention is shown and includes an elongated, hollow, cylindrically-shaped tubular member 21 having a proximal end 23, an open distal end 22, and a sidewall 25 extending between the proximal end 23 and the distal end 22 defining an internal chamber 26 having an internal reservoir 28. The sidewall 25 of tube 21 defines an internal surface 27 for slidably receiving a plunger assembly 30. An annular flange 24 is provided at the proximal end 23 of the tubular member 21 and extends from the internal surface 27 into chamber 26 partially closing the proximal end 23 of the tubular member 21.

Tubular member 21 may be made of one or more than one of the following representative materials: polypropylene, polyethylene, polyethyleneterephthalate (PET), polystyrene, polycarbonate, cellulosics, glass products, or combinations thereof. More expensive plastics such as polytetrafluoroethylene and other fluorinated polymers may also be used. In addition to the materials mentioned above, examples of other suitable materials include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF, and perfluoroalkoxy resins. One exemplary glass product is PYREX® (available from Corning Glass, Corning, N.Y.). Ceramic collection devices can be used according to embodiments of the invention. Cellulosic products such as paper and reinforced paper containers can also be used to form collection devices according to the invention.

With continuing reference to FIG. 3, the fluid collection cartridge 20 according to an embodiment of the invention further includes a plunger assembly 30 slidably received within the chamber 26 defined by sidewall 25 of the tube 21. The plunger assembly 30 includes a stopper 32 and a removable plunger rod 31. The stopper 32 is slidably positioned in fluid tight engagement with internal surface 27, and is able to slide distally and proximally along a longitudinal axis 29. The stopper 32 and plunger rod 31 are removably associated with one another by an interengaging arrangement, generally indicated as 90. The interengaging arrangement 90 is configured to enable the plunger rod 31 to apply a distally directed force to the stopper 32 and to enable removal of the plunger rod 31 from the stopper 32 and from the tubular member 21 upon the application of a proximally directed force, as shown by "P" in FIG. 7. In other words, the stopper 32 and plunger rod 31 are not mechanically secured to each other but merely are arranged in a removable contacting arrangement which only allows plunger rod 31 to exert a force in a distal direction on stopper 32. A proximal end 31a of the removable plunger rod 31 may include a thumb flange 33 that a user may use to exert a force to push the entire plunger assembly 30 distally, or pull to remove the plunger rod 31 from tubular member 21.

According to an embodiment of the invention as shown in FIG. 3, stopper 32 includes a distal face 34 and a proximal face 35. The diameter of stopper 32 is approximately equal to or only slightly smaller than the internal diameter 'a' of the tube 21 but is greater than the internal diameter 'b' of annular flange 24. Stopper 32 is in slidable contact with internal surface 27 of tube 21 and provides a fluid-tight seal between the plunger assembly 30 and the internal surface 27 of the tube 21 so that a sample can be held within the internal reservoir 28 formed within the chamber 26 between distal end 22 of tube 21 and distal face 34 of stopper 32, thereby preventing the sample from leaking from the proximal end 23 of tube 21.

Stopper 32 is a low resistance stopper and as such is designed to have a relatively lower frictional resistance to movement inside of tube 21 when compared to similar components in prior art arterial blood gas syringes such that the presence of fluid pressure, such as arterial blood pressure, within internal reservoir 28 will cause the stopper 32 to slide/travel in a proximal direction toward the proximal end 23 of tube 21 until the proximal face 35 of the stopper 32 contacts annular flange 24 thereby limiting the proximal movement of stopper 32. The frictional resistance of a stopper can be lowered by either a combination of stopper sealing profile design and/or component material selection. In the embodiment shown in FIG. 3, first 36 and second 37 sealing rings extend around the outer circumferential surface of stopper 32 near the distal face 34 and proximal face 35, respectively, to create a primary and secondary seal with internal surface 27 of tube 21. This stopper sealing profile design lowers the amount of contact between stopper 32 and internal surface 27 thereby reducing the frictional resistance to movement of stopper 32 when compared to a stopper sealing profile in which the entire outer circumferential surface is in contact with internal surface 27. Alternately or in combination with the stopper sealing profile design, stopper 32 is preferably made of an elastomeric material such as natural rubber, synthetic rubber, thermoplastic elastomers, and combinations thereof which are formulated or synthesized to be self-lubricating or have relatively lower frictional resistance. Stopper 32 may also be made from a combination of elastomers which include a harder inner rubber core and a soft self-lubricating polymeric material outer layer. A self-lubricating polymeric material has a lubricant such as silicone oil incorporated into the polymeric material, an example of which is Epilor.

Prior to use, plunger rod 31 contacts the proximal face 35 of stopper 32 in such a manner that plunger rod 31 can only impart a force applied in the distal direction. In the embodiment shown in FIG. 3, the interengaging arrangement 90 can include a male member, such as a conical finger 39, extending from a distal end 38 of plunger rod 31 which is configured to mate with a corresponding female member, such as a conical recess 45, in the proximal face 35 of stopper 32. It can be appreciated that the conical finger 39 and conical recess 45 illustrate one example of an interengaging arrangement 90 and that other interengaging arrangements can be used to removably connect the plunger rod 31 with the stopper 32. For example, the interengaging arrangement 90 can be designed such that the distal end 38 of the plunger rod 31 includes a female member configured to mate with a corresponding male member extending from the proximal face 35 of the stopper 32. In use and with reference to FIGS. 5-7, application of a force, such as by a user, to the thumb flange 33 causes plunger rod 31 to transmit the applied force to move stopper 32 in a distal direction to force fluids out of the blood collection cartridge should a fluid passageway be present in the distal end 22 of tube 21. However, pulling plunger rod 31 in a proximal direction, as shown by "P" in FIG. 7, will impart no force on stopper 32. Conical finger 39 will simply retract out of contact with recess 45, thus stopper 32 will remain stationary in tube 21 while plunger rod 31 is removed from tubular member 21.

Plunger rod 31 is desirably constructed of a suitable polymeric material, and may be manufactured by injection molding with a suitable polymer material known in the art. It is within the purview of the present invention to include plunger rods and stoppers which are separately formed or integrally formed of the same material or different materials such as in two-color molding, or separately formed of the same or different materials and joined together by mechanical means, adhesives, ultrasonic welding, heat sealing, or other suitable means.

Figure 4:
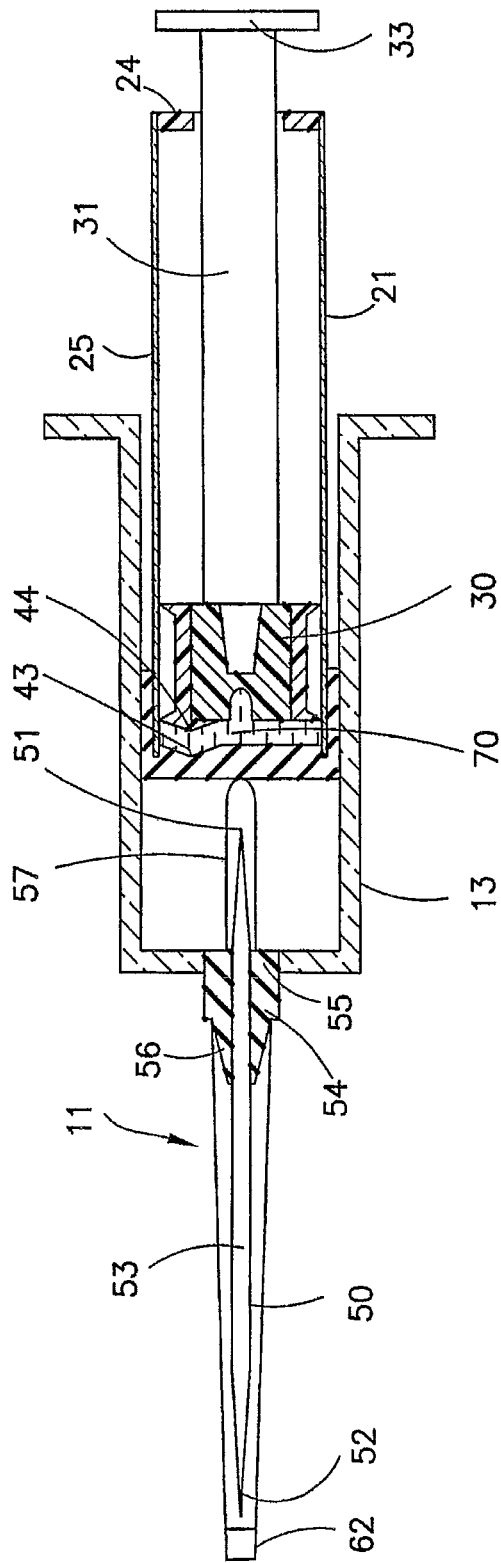
FIG. 4 is a cross-sectional side view of the fluid collection assembly as shown in FIG. 3 during the insertion of a fluid collection cartridge into the holder in accordance with an embodiment of the present invention.

With continuing reference to FIG. 3, a pierceable closure, generally indicated as 40, is associated with the open distal end 22 of the tubular member 21. The closure 40 is configured to cooperate with the sidewall 25 of the tubular member 21 to sealingly close the open distal end 22 to form a liquid impermeable seal to contain the fluid sample. The closure 40 includes an external end 41 and an internal end 42 structured to be at least partially received within the tubular member 21. Portions of the closure 40 adjacent the open distal end 22 of the tube 21 define a maximum outer diameter which exceeds the inside diameter 'a' of the tube 21. The inherent resiliency of closure 40 can ensure a sealing engagement with the internal surface 27 of the wall 25 of the tube 21. Portions of the closure 40 extending downwardly from the internal end 42 may taper from a minor diameter which is approximately equal to, or slightly less than, the inside diameter 'a' of the tube 21, to a major diameter that is greater than the inside diameter 'a' of the tube 21 adjacent the distal end 22. Thus, the internal end 42 of the closure 40 may be urged into a portion of the tube 21 adjacent the distal open end 22. Closure 40 is such that it can be pierced by a needle 50 or other cannula to introduce a biological sample into tubular member 21. According to one embodiment, closure 40 is resealable. The closure 40 can also be formed to define a cavity 43, as shown in FIG. 4, extending into the internal end 42. The cavity 43 may be sized to receive at least a corresponding mixing fin 44 extending distally from the distal face 34 of stopper 32. Alternatively, a plurality of cavities and corresponding mixing fins may be present. Suitable materials for closure 40 include, for example, elastomers such as silicone rubber, natural rubber, styrene butadiene rubber, ethylene-propylene copolymers and polychloroprene, thermoplastic elastomers, and the like.

According to an embodiment, the fluid collection cartridge 20 may contain additional additives as required for particular testing procedures, such as anticoagulants, clotting agents, stabilization additives, and the like, as illustrated as 70 in FIG. 4. Such additives may be sprayed onto the internal surface 27 of the tube 21 or located within the internal reservoir 28. The anticoagulants may include hirudins, hirudin derivatives, chelating agents, or chelating agent derivatives. Specific anticoagulants include citrate, ethylenediaminetetraacetic acid (EDTA), heparin, CPAD, CTAD, CPDA-1, CP2D, potassium oxalate, sodium fluoride, or ACD. The anticoagulant can be used in a liquid form to improve the incorporation, hence, effectiveness of the anticoagulant upon collection of arterial blood. The liquid form can be an emulsion, solution, or dispersion of the anticoagulant in a suitable carrier. Other known arterial blood sample collection methods use an arterial blood gas syringe preloaded upon manufacture with a solid form of anticoagulant such as heparin powder within the syringe barrel in order to maximize the shelf life of the syringe. The use of a solid form of anticoagulant can cause a reduction in the effectiveness of the anticoagulant as the incorporation of powdered heparin into the blood sample is difficult due to lack of agitation during the arterial blood collection process.

Figure 11:
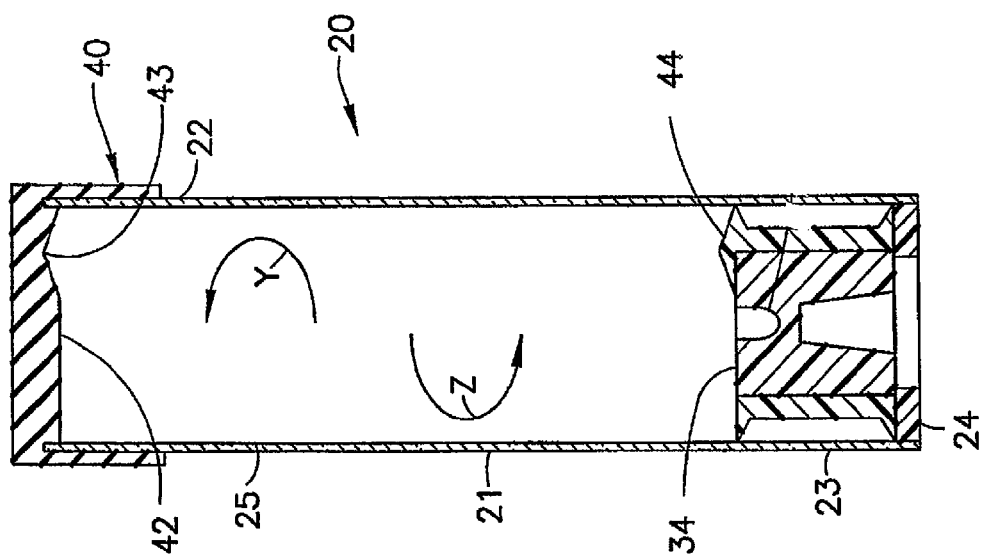
FIG. 11 is a cross-sectional side view of the fluid collection cartridge as shown in FIG. 9 showing the mixing dynamics after collection of a fluid sample in accordance with an embodiment of the present invention.
Figure 10:
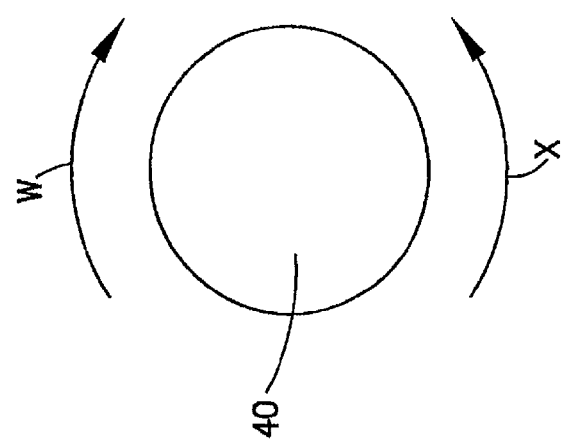
FIG. 10 is a plan view of the fluid collection cartridge as shown in FIG. 9 showing the direction of agitation after collection of a fluid sample in accordance with an embodiment of the present invention.

The combination of a cavity 43 in the internal end 42 of closure 40 and a mixing fin 44 extending from distal face 34 of stopper 32 provides asymmetric surfaces at each end of the fluid reservoir 28. As illustrated in FIGS. 10 and 11, when the cartridge 20 is rolled by rotating the cartridge about longitudinal axis in the direction of arrows w and x, the cavity 43 and mixing fin 44 create vortices that promote thorough mixing of the contents of the fluid reservoir 28. This is particularly useful in instances where there is no air (headspace) in the fluid reservoir of a collection vessel. Tipping such devices end-over-end does little to mix the contents, especially if the components are similar in density. Vessels with a cylindrical internal fluid reservoir such as vials, insulin pen cartridges, and syringes typically have flat internal surfaces in the top and bottom of the fluid reservoir. Therefore, little turbulence is created when these vessels are rolled.

With reference to FIGS. 1-2 and 4-7, an embodiment of a fluid collection system is shown including a needle assembly 11, and a holder 13. The needle assembly 11 includes a needle cannula 50 having a pointed proximal end 51, a pointed distal end 52, and a lumen 53 extending between the proximal end 51 and distal end 52. The needle assembly 11 further includes a hub 54 having a proximal end 55, a distal end 56, and a passage extending between the proximal end 55 and distal end 56. Portions of the needle cannula 50 extending between the proximal end 51 and distal end 52 are mounted securely in the passage of the hub 54. Thus, the pointed proximal end 51 of the needle cannula 50 projects proximally beyond the hub 54 and the pointed distal end of the needle cannula projects distally beyond the hub 54. External surface regions of the hub 54 near the proximal end 55 of the hub 54 may be formed with mounting structures, such as an array of external threads, at least one annular groove, or at least one annular rib. The mounting structure enables the needle hub 54 to be secured to a holder 13 that is configured to slidably receive a blood collection cartridge 20 according to an embodiment of the invention. The needle assembly 11 may further include a multiple sample sleeve 57, as shown in FIG. 4, mounted over the proximal portion of the needle cannula 50 and secured to the proximal end 55 of the hub 54. The proximal portions of the needle cannula 50 and the multiple sample sleeve 57 project into the holder 13 when the hub 54 of the needle assembly 11 is mounted to the holder 13.

Referring back to FIG. 1 and with continuing reference to FIGS. 2-7, according to an embodiment of the invention needle assembly 11 includes a first needle shield 60 and a second needle shield 61. First needle shield 60 covers distal end 52 of cannula 50 while second needle shield 61 covers the proximal end 51 of cannula 50. First needle shield 60 includes an indicator tip 62 at the distal end that is activated by the presence of a fluid treatment material 70, such as a liquid anticoagulant.

Assembly of the fluid collection cartridge 20 is accomplished by slidably inserting stopper 32 within chamber 26 through distal end 22 of tubular member 21. Fluid treatment material 70, such as liquid anticoagulant heparin, is then added to fluid reservoir 28 before distal end 22 is sealed by the insertion of closure 40. Plunger rod 31 is then inserted through annular flange 24 at proximal end 23 of tube 21 until conical finger 39 mates with recess 45. The assembly can then be packaged for later use.

Figure 5:
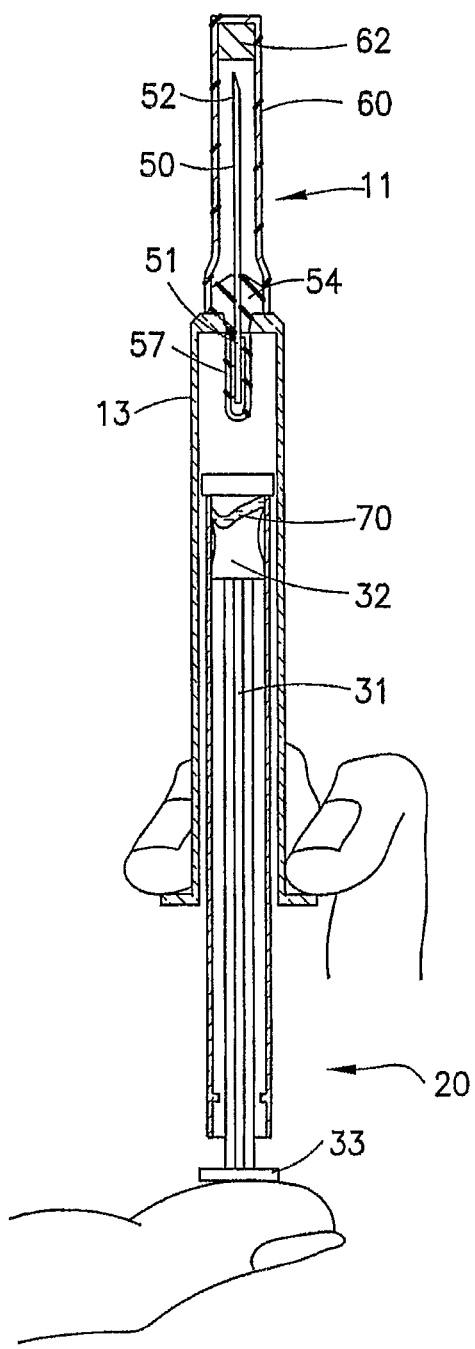
FIG. 5 is a cross-sectional side perspective view of the fluid collection assembly as shown in FIG. 2 during the insertion of the fluid collection cartridge into the holder in accordance with an embodiment of the present invention.

In a method of use according to an embodiment of the present invention, second needle shield 61 is removed from needle assembly 11 and holder 13 connected for fluid collection, such as for arterial blood collection. A fluid collection cartridge 20 in accordance with an embodiment of the invention, such as a blood collection cartridge, is then inserted into the proximal end of holder 13 as shown in FIGS. 4-6 until pointed proximal end 51 of needle 50 penetrates closure 40 and lumen 53 is in fluid communication with the fluid treatment material 70, such as liquid heparin anticoagulant, located in fluid reservoir 28.

Figure 6:
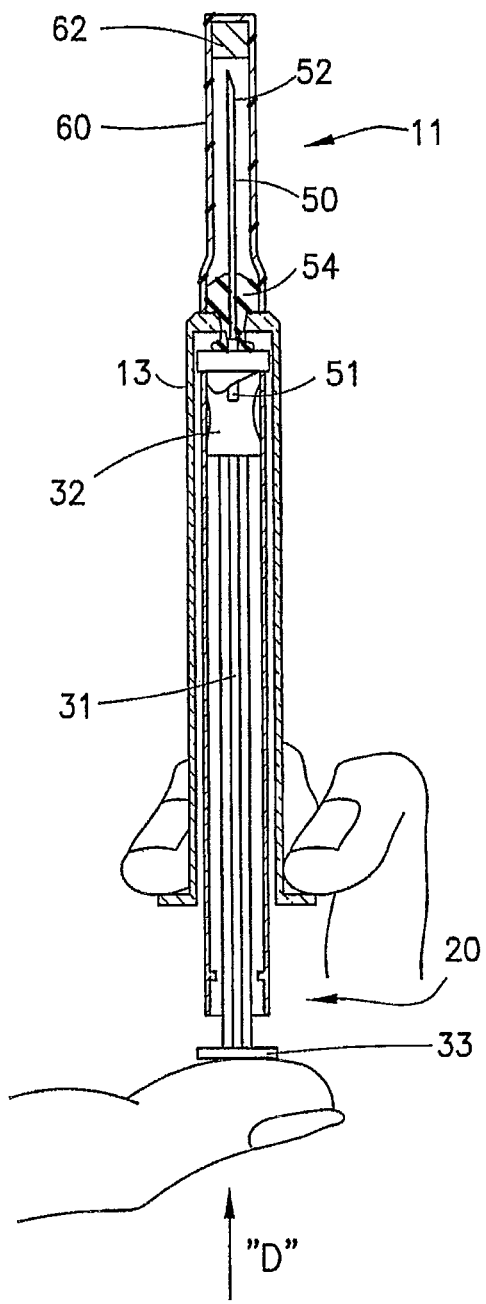
FIG. 6 is a cross-sectional side perspective view of the fluid collection assembly as shown in FIG. 2 after priming with a fluid treatment additive and prior to collection of a fluid sample in accordance with an embodiment of the present invention.
Figure 7:
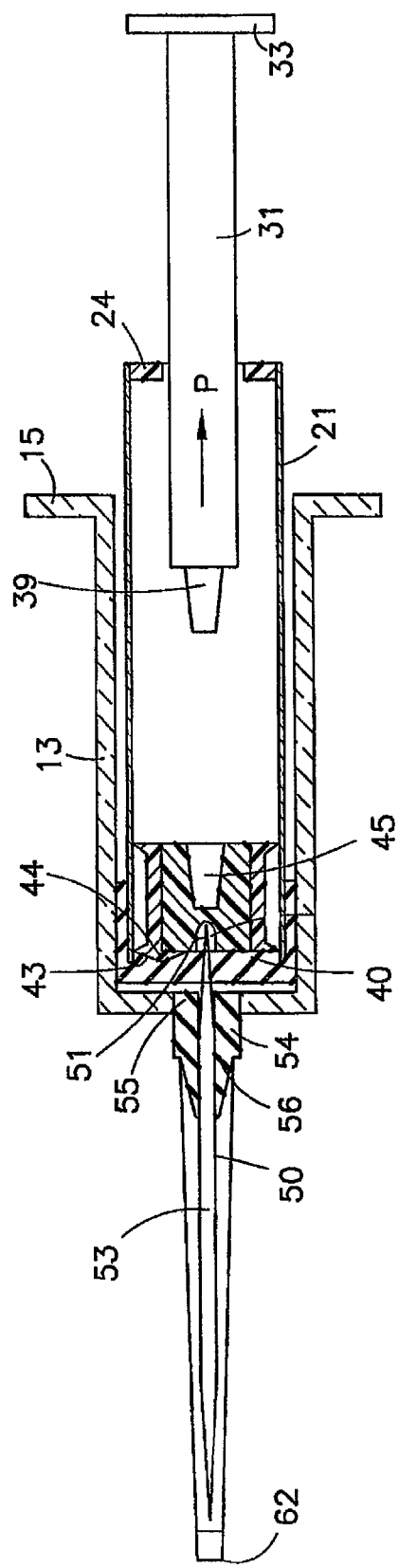
FIG. 7 is a cross-sectional side view of the fluid collection assembly as shown in FIG. 4 after priming with a fluid treatment additive and during the removal of the plunger rod in accordance with an embodiment of the present invention.

A user then grips the holder 13, anchors fingers about an outwardly extending annular flange 15 on the holder 13, and presses down upon thumb flange 33 with sufficient force in a distal direction "D", as shown in FIG. 6, until the distal face of stopper 32 contacts internal end 42 of closure 40 and the internal mixing fin 44 mates with recess 45 and proximal end 51 of cannula 50 is accommodated in cavity 43 of stopper 32, as shown in FIG. 7. This action causes the fluid treatment material 70 within the fluid collection cartridge 20 to flow from fluid reservoir 28 via proximal end 51 into lumen 53 of cannula 50 and into the first needle shield 60. The indicator tip 62 will activate and change color upon contact with the excess fluid treatment material as it is expelled from distal end 52 of needle 50, to give the user a visual confirmation that any dead space within fluid reservoir 28 or lumen 53 of the needle 50 is primed with the fluid treatment material 70. The plunger rod 31 can then be separated from the stopper 32 by pulling plunger rod 31 in a proximal direction (indicated by arrow P) as shown in FIG. 7. The residual volume (10-20 ul) of fluid treatment material 70 which is present in the dead space should be at a concentration so as to provide sufficient treatment, such as providing sufficient anticoagulant function to prevent clotting of an arterial blood sample upon collection.

The purpose of priming assembly 10 with a fluid treatment material is to remove any atmospheric air, so that the partial pressure of the oxygen, such as in an arterial blood sample, will not be affected by the atmospheric air. The assembly 10 should preferably have low dead space to keep the residual volume of the fluid treatment material low in order to minimize the dilution effect of the fluid treatment material on the fluid sample.

Figure 8:
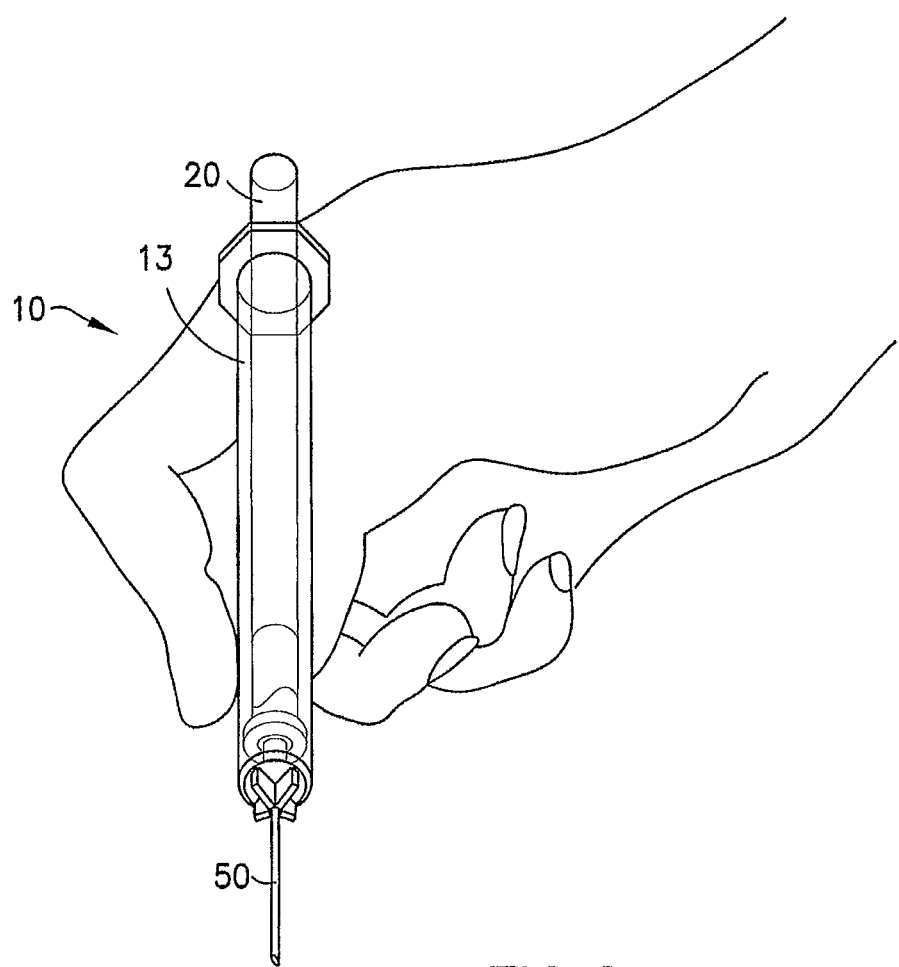
FIG. 8 is a perspective view of the fluid collection assembly as shown in FIG. 2 during fluid collection in accordance with an embodiment of the present invention.
Figure 9:
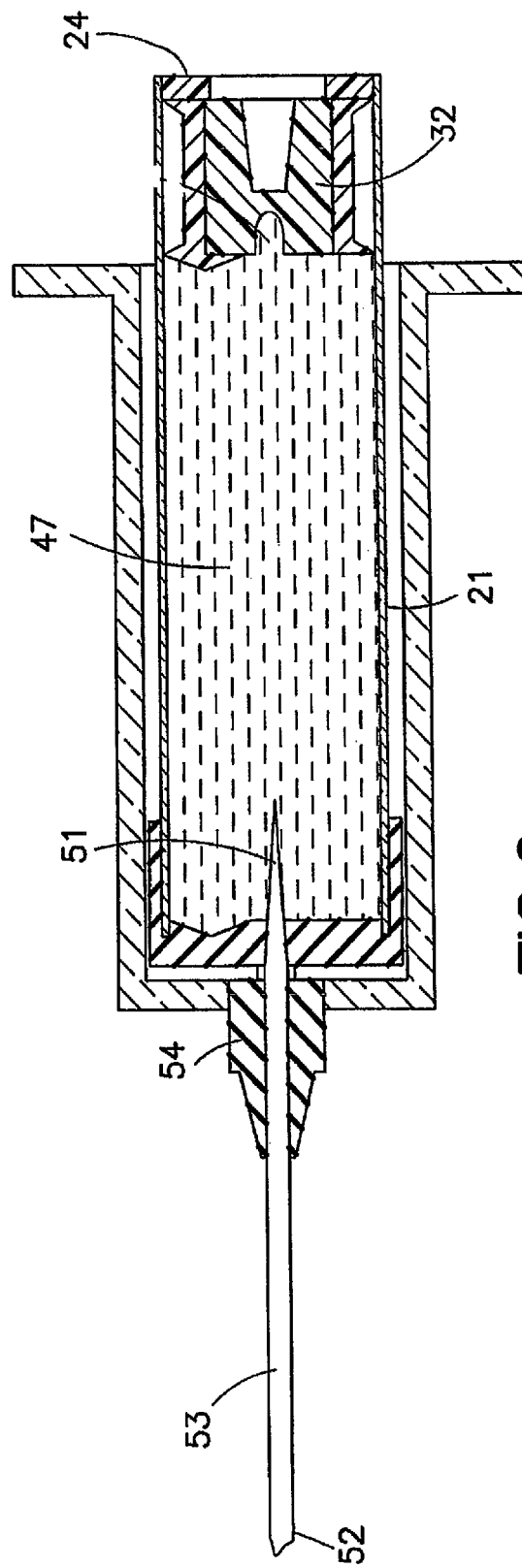
FIG. 9 is a cross-sectional side view of the fluid collection assembly as shown in FIG. 8 upon completion of collection of a fluid sample in accordance with an embodiment of the present invention.

A method of fluid collection according to an embodiment of this invention enables a single-handed technique similar to current clinical practice in the fluid collection process or an arterial blood collection process using a low resistance rubber stopper that is moved by the arterial pressure. First needle shield 60 is removed from needle assembly 11. The user grips assembly 10 as shown in FIG. 8 with one hand and inserts distal end 52 into a fluid source, such as a patient's artery. When using the invention to remove arterial blood, the blood at arterial pressure (which is greater than normal atmospheric or ambient pressure) will then flow through lumen 53 of cannula 50 into the fluid reservoir 28 and forces stopper 32 to slide in a proximal direction until the stopper proximal face 35 contacts annular flange 24 thereby defining the completion of the collection volume of the blood sample as shown in FIG. 9. The sliding motion of the rubber stopper 32 allows the fluid treatment material 70 and the collected arterial blood to mix, as shown at 47, during the collection process.

Fluid or blood collection cartridge 20 is then removed from the multi-sample needle assembly 11 and holder 13. The distal end 52 can then be removed from the fluid source or artery. The detached cartridge 20 may then be rolled between the user's palms in a plane perpendicular to longitudinal axis 29 in order to further mix the fluid sample with a fluid treatment material 70, such as heparin, as shown in FIGS. 10 and 11. The asymmetrical finned surfaces of the internal end 42 of closure 40 and the distal face 34 of stopper 32 create a vortex when the cartridge 20 is rolled in the directions as indicated by arrows w, x, y, and z. The fluid collection cartridge 20 containing the fluid sample is now ready for transportation to the laboratory such as for arterial blood gas analysis.

Figure 12:
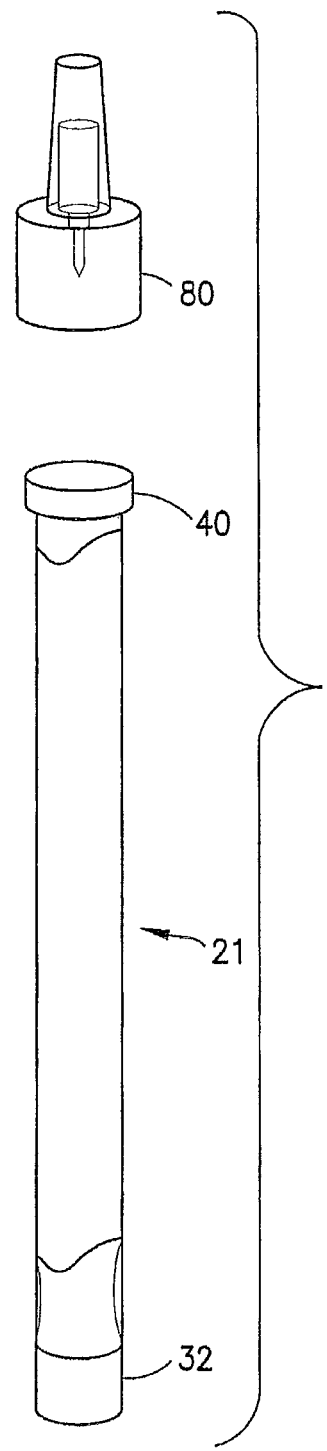
FIG. 12 is a perspective side view of the fluid collection cartridge as shown in FIG. 9 with a luer adapter in preparation for transportation and testing in accordance with an embodiment of the present invention.

According to one embodiment, a luer adapter 80 as shown in FIG. 12 may then be inserted through closure 40 of the cartridge 20 to provide the cartridge with an interface connection that is compatible with a blood gas analyzer. A range of different luer adapters can be provided to allow the fluid collection cartridge 20 to connect to all different types of testing equipment and/or all different types of blood gas analyzer interfaces. The luer adapter 80 may also be supplied with a luer tip cap (not shown) to seal the fluid collection cartridge 20 when the luer adapter 80 is connected.

While the present invention is satisfied by embodiments in many different forms, there is shown in the drawings and described herein in detail the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A fluid collection cartridge configured for use with a needle holder for collecting a fluid sample, the fluid collection cartridge comprising:
    a tubular member having a proximal end, an open distal end, and a sidewall extending between the proximal end and the distal end defining an internal chamber having an internal reservoir;
    a pierceable closure associated with the open distal end of the tubular member, the closure configured to cooperate with the sidewall of the tubular member to sealingly close said open distal end; and
    a plunger rod assembly including a stopper and a plunger rod removably associated with one another by an interengaging arrangement, wherein said interengaging arrangement is configured to enable the plunger rod to apply a distally directed force to the stopper and to enable removal of the plunger rod from the stopper and from the tubular member upon the application of only a proximally directed force, and further wherein the interengaging arrangement is configured to only enable the stopper to move in a distal direction based on force applied by the plunger rod,
    wherein the stopper comprises at least one mixing fin extending distally from a distal face of the stopper, and further wherein the pierceable closure comprises an internal end at least partially received within the tubular member and at least one cavity extending into the internal end of the pierceable closure, the cavity being sized to receive the at least one mixing fin of the stopper.

2. The fluid collection cartridge of claim 1, wherein said internal reservoir is configured to contain a fluid treatment additive.

3. The fluid collection cartridge of claim 2, wherein the fluid treatment additive comprises an anticoagulant in liquid form.

4. The fluid collection cartridge of claim 1, wherein the stopper is slidably positioned between the distal end and the proximal end of the tubular member in fluid-tight engagement with an inside surface of the sidewall.

5. The fluid collection cartridge of claim 1, wherein the stopper is a low resistance stopper.

6. The fluid collection cartridge of claim 1, wherein the stopper is configured to move toward the proximal end of the tubular member upon the collection of the fluid sample in the internal reservoir.

7. The fluid collection cartridge of claim 1, wherein the stopper includes at least one sealing ring extending around an outer circumferential surface of the stopper.

8. The fluid collection cartridge of claim 7, wherein the stopper includes a first sealing ring and a second sealing ring extending around the outer circumferential surface of the stopper.

9. The fluid collection cartridge of claim 1, wherein the proximal end of the tubular member includes an annular flange extending into the internal chamber.

10. The fluid collection cartridge of claim 1, wherein the interengaging arrangement comprises a male member extending from a distal end of the plunger rod and a corresponding female member in a proximal face of the stopper configured to mate with the male member of the plunger rod.

11. A fluid collection assembly comprising:
    (a) a fluid collection cartridge comprising:
        (i) a tubular member having a proximal end, an open distal end, and a sidewall extending between the proximal end and the distal end defining an internal chamber having an internal reservoir;
        (ii) a pierceable closure associated with the open distal end of the tubular member, the closure configured to cooperate with the sidewall of the tubular member to sealingly close the open distal end; and
        (iii) a plunger rod assembly including a stopper and a plunger rod removably associated with one another by an interengaging arrangement, wherein the interengaging arrangement is configured to enable the plunger rod to apply a distally directed force to the stopper and to enable removal of the plunger rod from the stopper and from the tubular member upon the application of only a proximally directed force, wherein the stopper comprises at least one mixing fin extending distally from a distal face of the stopper, and further wherein the pierceable closure comprises an internal end at least partially received within the tubular member and at least one cavity extending into the internal end of the pierceable closure, the cavity being sized to receive the at least one mixing fin of the stopper;

(b) a needle assembly including a cannula having a distal end and a proximal end and a first needle shield covering the distal end; and (c) a holder associated with the needle assembly, the holder configured for cooperating with the fluid collection cartridge for collecting a fluid sample.

12. The fluid collection assembly of claim 11, wherein the first needle shield includes an indicator tip.

13. The fluid collection assembly of claim 11, wherein the internal reservoir is configured to contain a fluid treatment additive.

14. The fluid collection assembly of claim 11, wherein the distal end of the cannula is configured to withdraw a blood sample from an artery and wherein the presence of arterial blood pressure in the internal reservoir during blood collection causes the stopper to move toward the proximal end of the tubular member.

15. A method of collecting a blood sample comprising:
(a) providing a fluid collection assembly comprising:
   (i) a fluid collection cartridge having:
      a tubular member having a proximal end, an open distal end, and a sidewall extending between the proximal end and the distal end defining an internal chamber having an internal reservoir;
      a pierceable closure associated with the open distal end of the tubular member, the closure configured to cooperate with the sidewall of the tubular member to sealingly close the open distal end; and
      a plunger rod assembly including a stopper and a plunger rod removably associated with one another by an interengaging arrangement, wherein the interengaging arrangement is configured to enable the plunger rod to apply a distally directed force to the stopper and to enable removal of the plunger rod from the stopper and from the tubular member upon the application of only a proximally directed force, wherein the stopper comprises at least one mixing fin extending distally from a distal face of the stopper, and further wherein the pierceable closure comprises an internal end at least partially received within the tubular member and at least one cavity extending into the internal end of the pierceable closure, the cavity being sized to receive the at least one mixing fin of the stopper;
   (ii) a needle assembly including a cannula having a distal end and a proximal end and a first needle shield covering the distal end; and
   (iii) a holder associated with the needle assembly, the holder configured for cooperating with the fluid collection cartridge;
(b) priming the fluid collection assembly with a fluid treatment additive;
(c) removing the plunger rod from the fluid collection cartridge;
(d) removing the first needle shield from the distal end of the cannula; and
(e) collecting a fluid sample into the internal reservoir.

16. The method of claim 15, wherein the fluid treatment additive is an anticoagulant in a liquid form.

17. The method of claim 15, wherein the first needle shield comprises an indicator tip.

18. The method of claim 17, wherein priming the fluid collection assembly further comprises:
inserting the fluid collection cartridge into the holder such that the proximal end of the cannula pierces the pierceable closure;
pushing the plunger rod assembly in a distal direction until the stopper contacts the pierceable closure; and
observing a color change in the indicator tip.

19. The method of claim 15, wherein collecting a fluid sample into the internal reservoir further comprises:
inserting the distal end of the needle assembly into a fluid source such that fluid flows into the internal reservoir and forces the stopper to travel in a proximal direction along a longitudinal axis of the tubular member;
removing the fluid collection cartridge from the holder when the stopper contacts an annular flange extending into the internal reservoir; and
removing the distal end of the needle assembly from the fluid source.

20. The method of claim 19, further comprising attaching a luer adapter to the distal end of the tubular member of the fluid collection cartridge.

21. The fluid collection cartridge of claim 1, wherein the distal face of the stopper and at least one mixing fin define an asymmetric surface configured to promote mixing of fluid contained in the internal reservoir.

22. The fluid collection assembly of claim 11, wherein the distal face of the stopper and at least one mixing fin define an asymmetric surface configured to promote mixing of fluid contained in the internal reservoir.

23. The method of claim 15, wherein the distal face of the stopper and at least one mixing fin define an asymmetric surface configured to promote mixing of fluid contained in the internal reservoir.

* * * * *